United States Patent [19]

Meyer et al.

[11] 4,136,187
[45] Jan. 23, 1979

[54] ANTIHYPERTENSIVE 2-AMINO-4,5-DIHYDROPYRIDINE DERIVATIVES

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Germany

[21] Appl. No.: 518,283

[22] Filed: Oct. 29, 1974

Related U.S. Application Data

[62] Division of Ser. No. 383,962, Jul. 30, 1973, Pat. No. 3,959,292.

[30] Foreign Application Priority Data

Aug. 12, 1972 [DE] Fed. Rep. of Germany ....... 2239815

[51] Int. Cl.$^2$ ........................................... A61K 31/455
[52] U.S. Cl. .................... 424/266; 424/246; 424/248.54; 424/248.55; 424/250
[58] Field of Search ........................................ 424/166

[56] References Cited

U.S. PATENT DOCUMENTS

| | | | |
|---|---|---|---|
| 3,441,648 | 4/1969 | Loev et al. | 260/295.5 R |
| 3,485,847 | 12/1969 | Bossert et al. | 260/295.5 R |
| 3,488,359 | 1/1970 | Bossert et al. | 260/295.5 R |
| 3,708,489 | 1/1973 | Rucker et al. | 260/295.5 R |
| 3,773,773 | 11/1973 | Bossert | 260/295.5 R |

*Primary Examiner*—Leonard Schenkman
*Attorney, Agent, or Firm*—Jacobs & Jacobs

[57] ABSTRACT

4,5-Dihydropyridines bearing an N,N-disubstituted amino group in the 2-position, carbonyl functions in the 3- and 5-positions and being optionally substituted in the 6-position by lower alkyl or phenyl and, in the 4-position by lower alkyl, phenyl, substituted phenyl or a heterocyclic group, are antihypertensive agents and coronary vessel dilators. The compounds, of which 2-pyrrolidino-6-methyl-4-(3-nitrophenyl)-4,5-dihydropyridine-3,5-dicarboxylic acid 3,5-diethyl ester is a representative embodiment, are prepared through condensation of an ylideneacetoacetic acid ester and a substituted 3,3-diaminoacrylate.

93 Claims, No Drawings

ANTIHYPERTENSIVE 2-AMINO-4,5-DIHYDROPYRIDINE DERIVATIVES

This is a division of application Ser. No. 383,962 filed July 30, 1973, now U.S. Pat. No. 3,959,262.

DETAILED DESCRIPTION

The present invention pertains to 2-amino-4,5-dihydropyridine derivatives, to processes for their production and use and to pharmaceutical compositions containing such compounds and useful as antihypertensive agents and coronary vessel dilators.

In particular, the present invention pertains to compounds of the formula:

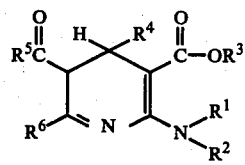

wherein $R^1$ when taken independently is hydrogen or lower alkyl;

$R^2$ when taken independently is lower alkyl or benzyl;

$R^1$ and $R^2$ when taken together, together with the nitrogen atom to which they are attached are a 5 to 7-membered saturated heterocyclic ring;

$R^3$ is lower alkyl, lower alkenyl or lower alkynyl;

$R^4$ is lower alkyl; lower alkenyl; lower alkynyl; phenyl; substituted phenyl in which the substituents are one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio or phenyl; naphthyl; or a heterocyclic ring selected from the group consisting of quinolyl, isoquinolyl, pyridyl, pyrimidyl, thenyl, furyl and pyrryl, said heterocyclic ring being unsubstituted or substituted by one or two members selected from the group consisting of lower alkyl, lower alkoxy and halogeno;

$R^5$ is lower alkyl, lower alkoxy, lower alkoxy(lower alkoxy), lower alkenyloxy, lower alkynyloxy, amino, lower alkylamino or di(lower alkyl)amino; and $R^6$ is hydrogen, lower alkyl or phenyl, and their non-toxic acid addition salts.

While the foregoing compounds have been depicted as 4,5-dihydropyridines, it is to be appreciated that the identical compounds can also be depicted as the fully equivalent tautomeric 3,4-dihydropyridines of the formula:

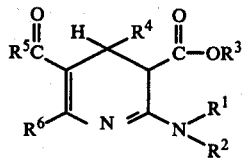

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.-pentyl, hexyl, and the like.

The term lower alkenyl denotes a univalent branched or straight hydrocarbon chain containing from 2 to 6 carbon atoms and ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and acetylenic unsaturation as, for example, ethynyl, 2-propynyl, 4-pentynyl, and the like.

The term lower alkoxy denotes a lower alkyl chain bound to the remainder of the molecule through an oxygen atom as, for example, methoxy, ethoxy, propoxy, isopropoxy, butoxy, isobutoxy, pentoxy and hexoxy.

The term lower alkylthio denotes a lower alkyl chain bound to the remainder of the molecule through a divalent sulfur as, for example, methylthio, ethylthio, propylthio, isopropylthio, butylthio, and the like.

The term halogen denotes the substituents fluoro, chloro, bromo and iodo.

The present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting an α-β-unsaturated dioxo compound of the formula:

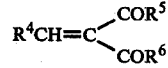

wherein $R^4$, $R^5$ and $R^6$ are as herein defined, with a substituted 3,3-diaminoacrylate of the formula:

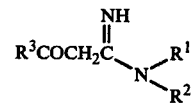

in which $R^1$, $R^2$ and $R^3$ are as herein defined. The condensation proceeds smoothly in good yields simply by heating the two components, generally in the presence of an inert organic solvent such as methanol, ethanol, propanol and similar alkanols, ethers such as dioxane and diethyl ether, glacial acetic acid, pyridine, dimethylformamide, dimethylsulfoxide, acetonitrile and the like. The reaction is conducted at temperatures of from 20° to 250° C., conveniently at the boiling point of the solvent, and while elevated pressure may be utilized, normal atmospheric pressure is generally satisfactory. The reactants are employed in substantially equimolar amounts. The diaminoacrylate reactant can be employed as the free base or in the form of a salt such as the hydrohalide salts with the free base being liberated from the salt through treatment with a basic agent such as an alkali metal alkoxide. The dicarbonyl reagent can be utilized as such or generated in situ by the reaction of an aldehyde of the formula $R^4CHO$ and a β-dicarbonyl compound of the formula $R^5COCH_2COR^6$.

It is rather surprising that the above described condensation produces the desired compounds in such good yields and with such high purity since it is known that a benzylideneacetoacetic acid ester condenses with an amino crotonic acid ester to yield 1,4-dihydropyridines (Knoevenagel, Ber. 31, 743, 1898). It is thus unexpected that the present reaction yields the 4,5- or 3,4-dihydropyridine derivatives exclusively rather than any 1,4-dihydropyridine derivatives.

Many of the α,β-unsaturated dioxo compounds utilized as one of the reactants are known to the art and the others can either be generated in situ as herein described or prepared according to methods well known to the art, see for example Org. Reaction XV, 204 et seq. (1967). Typical of this reactant are the following compounds:

benzylideneacetoacetic acid methyl ester,
ethylideneacetoacetic acid methyl ester,
isopropylideneacetoacetic acid methyl ester,
2-nitrobenzylideneacetoacetic acid methyl ester,
2-nitrobenzylideneacetylacetone,
benzylideneacetylacetone,
3-nitrobenzylideneacetoacetic acid methyl ester,
3-nitrobenzylideneacetoacetic acid propargyl ester,
3-nitrobenzylideneacetoacetic acid allyl ester,
3-nitrobenzylideneacetoacetic acid β-methoxyethyl ester,
3-nitrobenzylideneacetoacetic acid β-ethoxyethyl ester,
3-nitrobenzylideneacetoacetic acid isopropyl ester,
3-nitrobenzylideneacetylacetone,
4-nitrobenzylideneacetylacetone,
4-nitrobenzylideneacetoacetic acid β-propoxyethyl ester,
4-nitrobenzylideneacetoacetic acid n-propyl ester,
3-nitro-6-chlorobenzylideneacetoacetic acid methyl ester,
2-cyanobenzylideneacetoacetic acid methyl ester,
2-cyanobenzylideneacetoacetic acid methyl ester,
2-cyanobenzylideneacetoacetic acid ethyl ester,
2-cyanobenzylidenepropionylacetic acid ethyl ester,
3-cyanobenzylideneacetoacetic acid methyl ester,
3-nitro-4-chlorobenzylideneacetylacetone,
3-nitro-4-chlorobenzylideneacetoacetic acid t-butyl ester,
3-nitro-4-chlorobenzylideneacetoacetic acid methyl ester,
2-nitro-4-methoxybenzylideneacetoacetic acid methyl ester,
2-cyano-4-methylbenzylideneacetoacetic acid ethyl ester,
2-azidobenzylideneacetoacetic acid ethyl ester,
3-azidobenzylideneacetylacetone,
2-methylmercaptobenzylideneacetoacetic acid isopropyl ester,
2-sulphinylmethylbenzylideneacetoacetic acid ethyl ester,
2-sulphonylbenzylidenemethylacetoacetic acid allyl ester,
4-sulphonylmethylbenzylideneacetoacetic acid ethyl ester,
naphth-1-ylideneacetoacetic acid methyl ester,
naphth-1-ylideneacetoacetic acid ethyl ester,
naphth-2-ylideneacetoacetic acid ethyl ester,
2-ethoxynaphth-1-ylideneacetoacetic acid methyl ester,
2-methoxynaphth-1-ylideneacetoacetic acid ethyl ester,
5-bromonaphth-1-ylideneacetoacetic acid methyl ester,
quinol-2-ylmethylideneacetoacetic acid methyl ester,
quinol-3-ylmethylideneacetoacetic acid methyl ester,
quinol-4-ylmethylideneacetoacetic acid ethyl ester,
quinol-8-ylmethylideneacetoacetic acid ethyl ester,
isoquinol-1-ylmethylideneacetoacetic acid methyl ester,
isoquinol-3-ylmethylidene-acetoacetic acid methyl ester,
α-pyridylmethylideneacetoacetic acid methyl ester,
α-pyridylmethylideneacetoacetic acid ethyl ester,
α-pyridylmethylideneacetoacetic acid allyl ester,
α-pyridylmethylideneacetoacetic acid cyclohexyl ester,
β-pyridylmethylideneacetoacetic acid β-methoxyethyl ester,
γ-pyridylmethylideneacetoacetic acid methyl ester,
6-methyl-α-pyridylmethylideneacetoacetic acid ethyl ester,
4,6-dimethoxypyrimid-5-ylmethylideneacetoacetic acid ethyl ester,
then-2-ylmethylideneacetoacetic acid ethyl ester,
fur-2-ylmethylideneacetoacetic acid allyl ester,
pyrr-2-ylthylideneacetoacetic acid methyl ester,
nitrobenzylidenepropionylacetic acid ethyl ester,
α-pyridylmethylidenepropionylacetic acid ethyl ester,
α-pyridylmethylidenepropionylacetic acid methyl ester,
α-pyridylmethylideneacetylacetone,
2-, 3- or 4-methoxybenzylideneacetoacetic acid ethyl ester,
2-, 3- or 4-methoxybenzylideneacetylacetone,
2-methoxybenzylideneacetoacetic acid allyl ester,
2-methoxybenzylideneacetoacetic acid allyl ester,
2-methoxybenzylideneacetoacetic acid propargyl ester,
2-methoxybenzylideneacetoacetic acid β-methoxyethyl ester,
2-isopropoxybenzylideneacetoacetic acid ethyl ester,
3-butoxybenzylideneacetoacetic acid methyl ester,
3,4,5-trimethoxybenzylideneacetoacetic acid allyl ester,
2-methylbenzylidenepropionylacetic acid methyl ester,
2-, 3- or 4-methylbenzylideneacetoacetic acid ethyl ester,
2-methylbenzylideneacetoacetic acid β-methoxyethyl ester,
2-methylbenzylideneacetoacetic acid β-propoxyethyl ester,
2-methylbenzylideneacetylacetone,
3,4-dimethoxy-5-bromobenzylideneacetoacetic acid ethyl ester,
2-, 3- or 4-chlorobenzylideneacetoacetic acid ethyl ester,
2-, 3- or 4-bromobenzylideneacetoacetic acid ethyl ester,
2-, 3- or 4-fluorobenzylideneacetoacetic acid ethyl ester,
2-fluorobenzylideneacetoacetic acid ethyl ester,
3-chlorobenzylideneacetylacetone,
3-chlorobenzylidenepropionylacetic acid ethyl ester,
3-chlorobenzylideneacetoacetic acid ethyl ester,
2-chlorobenzylideneacetoacetic acid allyl ester,
2-, 3- or 4-trifluoromethylbenzylideneacetoacetic acid isopropyl ester,
3-trifluoromethylbenzylideneacetoacetic acid methyl ester,
2-carbethoxybenzylideneacetoacetic acid ethyl ester,
3-carbomethoxybenzylideneacetoacetic acid methyl ester,
4-carboisopropoxybenzylideneacetoacetic acid isopropyl ester, and
4-carbomethoxybenzylideneacetoacetic acid methyl ester.

The substituted 3,3-diaminoacrylates are readily produced from the appropriate cyanoacetic acid imino ester [see Cope, J.A.C.S. 67, 1017 (1945)] and a primary or secondary amine. This reaction may be depicted for example as follows:

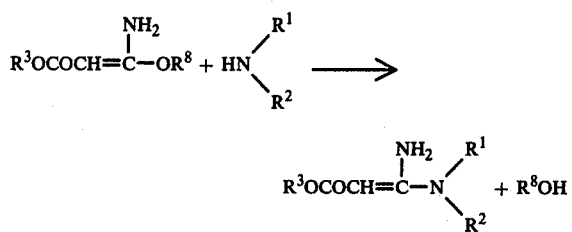

In the above, $R^1$, $R^2$ and $R^3$ are as herein defined and $R^8$ is lower alkyl.

Typical of these starting materials are:

3-methylamino-3-aminoacrylic acid ethyl ester,
3-dimethylamino-3-aminoacrylic acid methyl ester,
3-dimethylamino-3-aminoacrylic acid ethyl ester,
3-dimethylamino-3-aminoacrylic acid butyl ester,
3-benzylamino-3-aminoacrylic acid isopropyl ester,
3-isopropylamino-3-aminoacrylic acid ethyl ester,
3-ethylmethylamino-3-aminoacrylic acid methyl ester,
3-N-pyrrolidino-3-aminoacrylic acid ethyl ester,
3-N-pyrrolidino-3-aminoacrylic acid propyl ester,
3-N-pyrrolidino-3-aminoacrylic acid isopropyl ester,
3-N-piperidino-3-aminoacrylic acid ethyl ester,
3-N,N'-methylpiperazino-3-aminoacrylic acid ethyl ester,
3-N-morpholino-3-aminoacrylic acid ethyl ester,
3-N-thiamorpholino-3-aminoacrylic acid methyl ester,
3N-perhydroazepino-3-aminoacrylic acid ethyl ester,
and 3-N-pyrrolidino-3-aminoacrylic acid ethyl ester.

The compounds of the present invention and their preparation are herein described in terms of the broadest parameters envisioned. All subcombinations of the substituents are specifically included, it being apparent that any narrower definitions falling within the broad definitions of any of the substituents $R^1$, $R^2$, $R^3$, $R^4$, $R^5$ and $R^6$ and all combinations thereof are implicit alternative expressions of embodiments of the invention. Thus, for example, the substituents $R^1$ and $R^2$ can be envisioned as embracing open chain secondary and tertiary alkyl amines ($R^1$ is hydrogen or alkyl and $R^2$ is alkyl) or cyclic amines in which $R^1$ and $R^2$ are either alkylene of 4 to 7 carbon atoms or, together with the nitrogen atom to which they are attached a heterocyclic amine containing a further heteroatom such as piperazino, N-(lower alkyl)piperazino, morpholino, thiamorpholino and the like.

A preferred group of compounds are those of the formula:

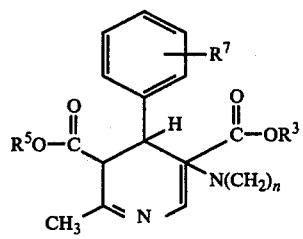

wherein each of $R^3$ and $R^5$ is lower alkyl, allyl or propargyl;
$R^7$ is hydrogen, chloro, nitro, cyano, trifluoromethyl, methyl, methoxy, or methylthio; and
n is 4, 5 or 6.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example the coronary vessel dilation effect can be observed by measuring the dose at which there is a distinctly discernible increase in oxygen saturation in the coronary sinus in the narcotized, heart catheterized dog, as shown in the following table:

| Compound | I.V. Dose (mg/kg) | Return to normal $O_2$ values (min) |
|---|---|---|
| 2-pyrrolidino-6-methyl-4-(3-nitrophenyl)-4,5-dihydropyridine-3,5-dicarboxylic acid 3-ethyl-5-methyl ester | 5 | >240 |
| 2-piperidino-6-methyl-4-(2-cyanophenyl)-4,5-dihydropyridine-3,5-dicarboxylic acid diethyl ester | 3 | 20 |
| 2-piperidino-6-methyl-4-(3-nitrophenyl)-4,5-dihydropyridine-3,5-dicarboxylic acid diethyl ester | 3 | 10 |
| 2-pyrrolidino-6-methyl-4-(2-trifluoromethylphenyl)-4,5-dihydropyridine-3,5-dicarboxylic acid diethyl ester | 2 | >240 |

The hypotensive activity of the present compounds can be observed by measuring the blood pressure of hypertensive rats following oral administration of the compounds. The following table demonstrates the dose which results in at least a 15 mm Hg reduction in blood pressure of such animals:

| Compound | Dose (mg/kg) | Oral Toxicity (mg/kg) |
|---|---|---|
| 2-pyrrolidino-6-methyl-4-(2-chlorophenyl)-4,5-dihydropyridine-3,5-dicarboxylic acid diethyl ester | 10.0 | >3000 |
| 2-pyrrolidino-6-methyl-4-(2-methoxyphenyl)-4,5-dihydropyridine-3,5-dicarboxylic acid diethyl ester | 31.5 | 2000 |
| 2-piperidino-6-methyl-4-(2-cyanophenyl)-4,5-dihydropyridine-3,5-dicarboxylic acid diethyl ester | 3.0 | >3000 |
| 2-pyrrolidino-6-methyl-4-(2-trifluoromethylphenyl)-4,5-dihydropyridine-3,5-dicarboxylic acid diethyl ester | 0.1 | >3000 |
| 2-pyrrolidino-6-methyl-4-(3-nitrophenyl)-4,5-dihydropyridine-3,5-dicarboxylic acid 3-ethyl ester-5-methyl ester | 3.0 | >3000 |
| 2-pyrrolidino-6-methyl-4-(2-cyanophenyl)-4,5-dihydropyridine-3,5-dicarboxylic acid diethyl ester | 1.0 | >3000 |
| 2-pyrrolidine-6-methyl-4-(3-nitrophenyl)-4,5-dihydropyridine-3,5-dicarboxylic acid 3-ethyl ester 5-isopropyl ester | 3.0 | >3000 |

The toxicity of the compounds is remarkably low as can be seen from the above.

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5%, of at least one 2-amino-4,5-dihydropyridine as herein defined in combination with a pharmaceutical carrier, the carrier comprising one or more solid, semisolid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.5 to about 4.5 g/kg, preferably 5 to 900 mg/kg, when administered parenterally and from about 2.5 to about 9.0 g/kg, preferably 5 to 900 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alignate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of the present invention through the presentation of specific embodiments. These examples should

EXAMPLE 1

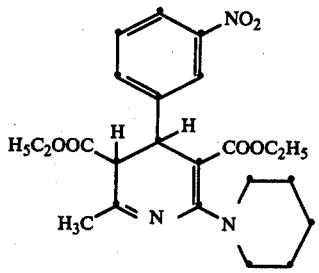

Boiling a solution of 13.2 g of 3-nitrobenzylideneacetoacetic acid ethyl ester and 9.9 g of 3-piperidino-3-aminoacrylic acid ethyl ester in 100 ml of ethanol for 2 hours yields 2-piperidino-6-methyl-4-(3-nitrophenyl)-4,5-dihydropyridine-3,5-dicarboxylic acid diethyl ester of melting point 80° C. (ether).

Yield: 68% of theory.

EXAMPLE 2

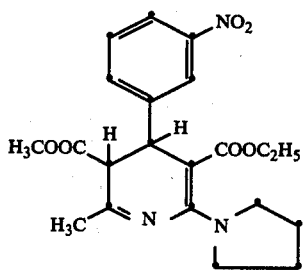

Boiling a solution of 12.5 g of 3-nitrobenzylideneacetoacetic acid methyl ester and 9.2 g of 3-pyrrolidino-3-aminoacrylic acid ethyl ester in 100 ml of ethanol for 2 hours yields 2-pyrrolidino-6-methyl-4-(3-nitrophenyl)-4,5-dihydropyridine-3,5-dicarboxylic acid 3-ethyl ester-5-methyl ester of melting point 103° C. (isopropanol/ether).

Yield: 74% of theory.

EXAMPLE 3

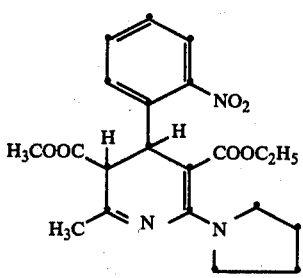

Boiling a solution of 12.5 g of 2-nitrobenzylideneacetoacetic acid methyl ester and 9.2 g of 3-pyrrolidino-3-aminoacrylic acid ethyl ester in 80 ml of ethanol for 2 hours yields 2-pyrrolidino-6-methyl-4-(2-nitrophenyl)-4,5-dihydropyridine-3,5-dicarboxylic acid 3-ethyl ester-5-methyl ester of melting point 132° C. (ethyl acetate/petroleum ether).

Yield: 53% of theory.

EXAMPLE 4

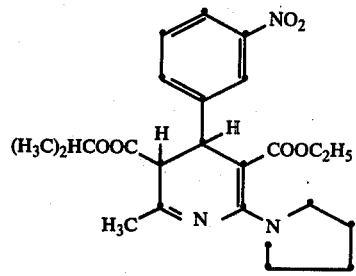

Boiling a solution of 13.9 g of 3-nitrobenzylideneacetoacetic acid isopropyl ester and 9.2 g of 3-pyrrolidino-3-aminoacrylic acid ethyl ester in 80 ml of ethanol for 2 hours yields 2-pyrrolidino-6-methyl-4-(3-nitrophenyl)-4,5-dihydropyridine-3,5-dicarboxylic acid 3-ethyl ester-5-isopropyl ester of melting point 105° C. (isopropanol/ester).

Yield: 64% of theory.

EXAMPLE 5

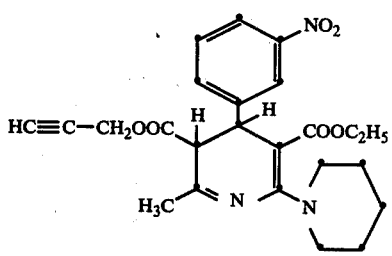

Boiling a solution of 13.6 g of 3-nitrobenzylideneacetoacetic acid propargyl ester and 9.9 g of 3-piperidino-3-aminoacrylic acid ethyl ester in 100 ml of ethanol for 2 hours yields 2-piperidino-6-methyl-4-(3-nitrophenyl)-4,5-dihydropyridine-3,5-dicarboxylic acid 3-ethyl ester-5-propargyl ester of melting point 121° C. (isopropanol).

Yield: 77% of theory.

EXAMPLE 6

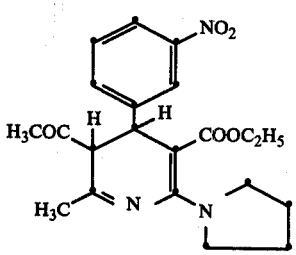

Heating a solution of 7.6 g of 3-nitrobenzaldehyde, 5.0 g of acetylacetone and 9.2 g of 3-pyrrolidino-3-aminoacrylic acid ethyl ester in 50 ml of ethanol for 2 hours yields 2-pyrrolidino-6-methyl-4-(3-nitrophenyl)-5-acetyl-4,5-dihydropyridine-3-carboxylic acid ethyl ester of melting point 130° C. (isopropanol/ether).

Yield: 44% of theory.

EXAMPLE 7

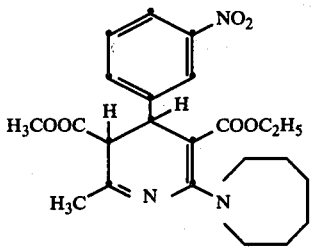

Heating a solution of 12.5 g of 3-nitrobenzylideneacetoacetic acid methyl ester and 10.6 g of 3-perhydroazepino-3-aminoacrylic acid ethyl ester in 100 ml of ethanol for 2 hours yields 2-perhydroazepino-6-methyl-4-(3-nitrophenyl)-4,5-dihydropyridine-3,5-dicarboxylic acid 3-ethyl ester-5-methyl ester of melting point 111° C. (ether).

Yield: 76% of theory.

EXAMPLE 8

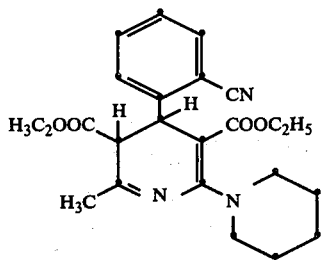

Boiling a solution of 12.2 g of 2-cyanobenzylideneacetoacetic acid ethyl ester and 9.9 g of 3-piperidino-3-aminoacrylic acid ethyl ester in 100 ml of ethanol for 2 hours yields 2-piperidino-6-methyl-4-(2-cyanophenyl)-4,5-dihydropyridine-3,5-dicarboxylic acid diethyl ester of melting point 103° C. (isopropanol).

Yield: 58% of theory.

EXAMPLE 9

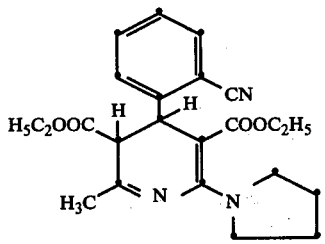

Boiling a solution of 12.2 g of 2-cyanobenzylideneacetoacetic acid ethyl ester and 9.2 g of 3-pyrrolidino-3-aminoacrylic acid ethyl ester in 100 ml of ethanol for 2 hours yields 2-pyrrolidino-6-methyl-4-(2-cyanophenyl)-4,5-dihydropyridine-3,5-dicarboxylic acid diethyl ester of melting point 115° C. (isopropanol).

Yield: 67% of theory.

EXAMPLE 10

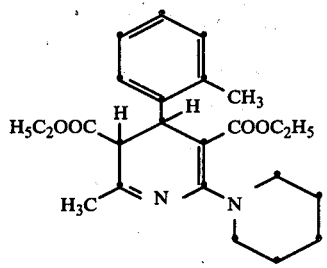

Heating a solution of 11.6 g of 2-methylbenzylideneacetoacetic acid ethyl ester and 9.9 g of 3-piperidino-3-aminoacrylic acid ethyl ester in 100 ml of ethanol for 2 hours yields 2-piperidino-6-methyl-4-(2-methylphenyl)-4,5-dihydropyridine-3,5-dicarboxylic acid diethyl ester of melting point 60° C. (ether/petroleum ether).

Yield: 47% of theory.

EXAMPLE 11

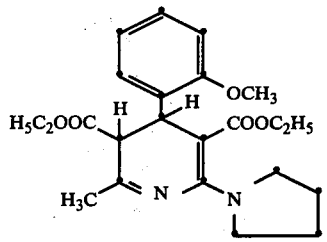

Boiling a solution of 12.4 g of 2-methoxybenzylideneacetoacetic acid ethyl ester and 9.2 g of 3-pyrrolidino-3-aminoacrylic acid ethyl ester in 100 ml of ethanol for 2 hours yields 2-pyrrolidino-6-methyl-4-(2-methoxyphenyl)-4,5-dihydropyridine-3,5-dicarboxylic acid diethyl ester of melting point 74° C. (ether).

Yield: 61% of theory.

EXAMPLE 12

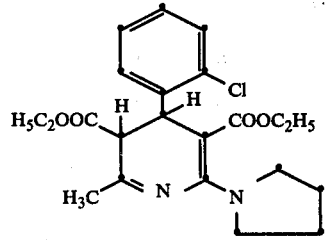

Heating a solution of 12.6 g of 2-chlorobenzylideneacetoacetic acid ethyl ester and 9.2 g of 3-pyrrolidino-3-aminoacrylic acid ethyl ester in 100 ml of ethanol for 2 hours yields 2-pyrrolidino-6-methyl-4-(2-chlorophenyl)-4,5-dihydropyridine-3,5-dicarboxylic acid diethyl ester of melting point 81° C. (ether/petroleum ether).

Yield: 53% of theory.

EXAMPLE 13

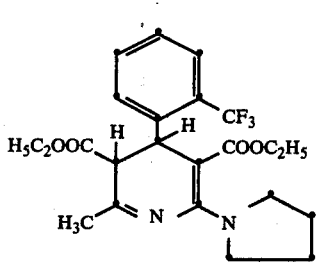

Boiling a solution of 14.3 g of 2-trifluoromethylbenzylideneacetoacetic acid ethyl ester and 9.2 g of 3-pyrrolidino-3-aminoacrylic acid ethyl ester in 100 ml of ethanol for 2 hours yields 2-pyrrolidino-6-methyl-4-(2-trifluoromethylphenyl)-4,5-dihydropyridine-3,5-dicarboxylic acid diethyl ester of melting point 98° C. (ether/petroleum ether).

Yield: 61% of theory.

EXAMPLE 14

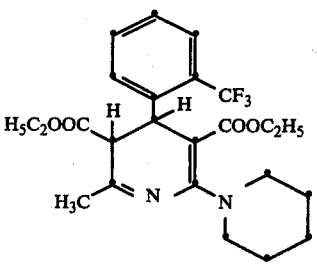

Boiling a solution of 14.3 g of 2-trifluoromethylbenzylideneacetoacetic acid ethyl ester and 9.9 g of 3-piperidino-3-aminoacrylic acid ethyl ester in 80 ml of ethanol for 2 hours yields 2-piperidino-6-methyl-4-(2-trifluoromethylphenyl)-4,5-dihydropyridine-3,5-dicarboxylic acid diethyl ester of melting point 80° C. (ether/petroleum ether).

Yield: 81% of theory.

EXAMPLE 15

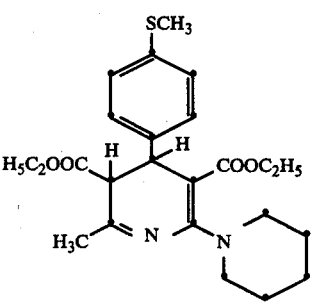

Boiling a solution of 13.2 g of 4-methylmercaptobenzylideneacetoacetic acid ethyl ester and 9.9 g of 3-piperidino-3-aminoacrylic acid ethyl ester in 80 ml of ethanol for 2 hours yields 2-piperidino-6-methyl-4-(4-methylmercaptophenyl)-4,5-dihydropyridine-3,5-dicarboxylic acid diethyl ester of melting point 100° C. (isopropanol-petroleum ether).

Yield: 54% of theory.

EXAMPLE 16

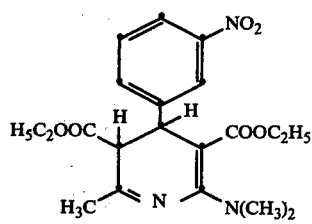

Boiling a solution of 13.2 g of 3-nitrobenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(3-nitrophenyl)-4,5-dihydropyridine-3,5-dicarboxylic acid diethyl ester of melting point 76° C. (ethyl acetate/petroleum ether).

Yield: 76% of theory.

EXAMPLE 17

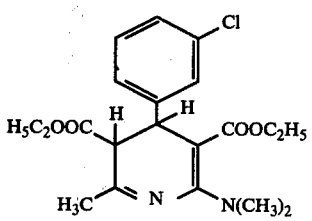

Boiling a solution of 12.6 g of 3-chlorobenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(3-chlorophenyl)-4,5-dihydropyridine-3,5-dicarboxylic acid diethyl ester of melting point 79° C. (isopropanol).

Yield: 59% of theory.

EXAMPLE 18

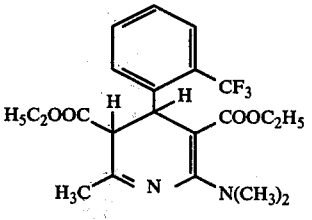

Boiling a solution of 14.3 g of 2-trifluoromethylbenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(2-trifluoromethylphenyl)-4,5-dihydropyridine-3,5-dicarboxylic acid diethyl ester of melting point 87° C. (isopropanol).

Yield: 62% of theory.

EXAMPLE 19

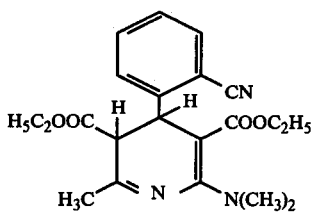

Boiling a solution of 12.2 g of 2-cyanobenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(2-cyanophenyl)-4,5-dihydropyridine-3,5-dicarboxylic acid diethyl ester of melting point 129° C. (isopropanol).

Yield: 56% of theory.

EXAMPLE 20

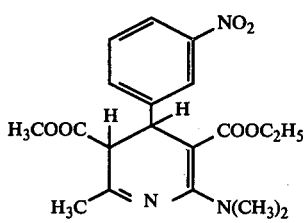

Boiling a solution of 12.5 g of 3-nitrobenzylideneacetoacetic acid methyl ester and 8.2 g of 3-amino-3-dimethylaminoacrylic acid ethyl ester in 100 ml of ethanol for 2 hours yields 2-dimethylamino-6-methyl-4-(3-nitrophenyl)-4,5-dihydropyridine-3,5-dicarboxylic acid 3-ethyl ester-5-methyl ester of melting point 95° C. (isopropanol).

Yield: 54% of theory.

EXAMPLE 21

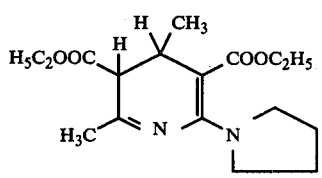

Boiling a solution of 7.8 g of ethylideneacetoacetic acid ethyl ester and 9.2 g of 3-pyrrolidino-3-aminoacrylic acid ethyl ester in 100 ml of ethanol for 2 hours and distilling the residue yields 2-pyrrolidino-4,6-dimethyl-4,5-dihydropyridine-3,5-dicarboxylic acid diethyl ester of boiling point (1.5 mm. Hg: 199°-204° C.).

Yield: 42% of theory.

EXAMPLE 22

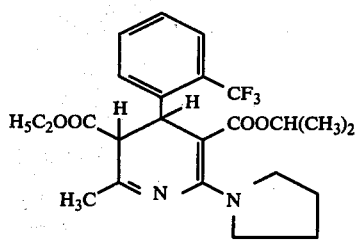

Boiling a solution of 14.3 g of 2-trifluoromethylbenzylideneacetoacetic acid ethyl ester and 9.9 g of 3-pyrrolidino-3-aminoacrylic acid isopropyl ester in 100 ml of ethanol for 2 hours yields 2-pyrrolidino-6-methyl-4-(2-trifluoromethylphenyl)-4,5-dihydropyridine-3,5-dicarboxylic acid 3-isopropyl ester-5-ethyl ester of melting point 102° C. (ethanol).

Yield: 55% of theory.

EXAMPLE 23

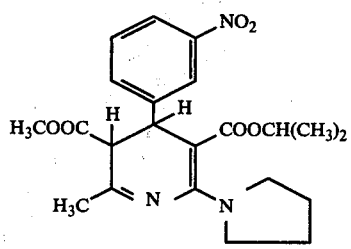

Boiling a solution of 12.5 g of 3-nitrobenzylideneacetoacetic acid methyl ester and 9.9 g of 3-pyrrolidino-3-aminoacrylic acid isopropyl ester in 100 ml of ethanol for 2 hours yields 2-pyrrolidino-6-methyl-4-(3-nitrophenyl)-4,5-dihydropyridine-3,5-dicarboxylic acid 3-isopropyl ester-5-methyl ester of melting point 140° C. (ethanol).

Yield: 64% of theory.

EXAMPLE 24

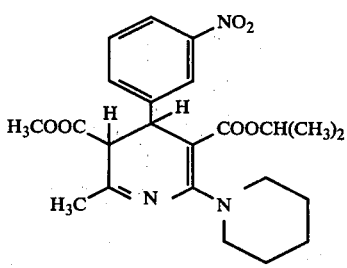

Boiling a solution of 12.5 g of 3-nitrobenzylideneacetoacetic acid methyl ester and 10.6 g of 3-piperidino-3-aminoacrylic acid isopropyl ester in 100 ml of ethanol for 2 hours yields 2-piperidino-6-methyl-4-(3-nitrophenyl)-4,5-dihydropyridine-3,5-dicarboxylic acid 3-isopropyl ester-5-methyl ester of melting point 112° C. (ethanol).

Yield: 59% of theory.

EXAMPLE 25

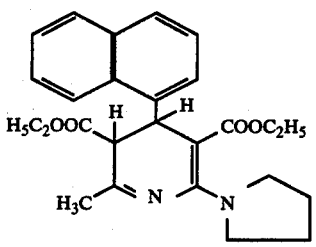

Boiling a solution of 13.4 g of naphth-1-ylmethylideneacetoacetic acid ethyl ester and 9.2 g of 3-pyrrolidino-3-aminoacrylic acid ethyl ester in 100 ml of ethanol for 2 hours yields 2-pyrrolidino-6-methyl-4-naphth-1-yl-4,5-dihydropyridine-3,5-dicarboxylic acid diethyl ester of melting point 121° C. (ethanol).

Yield: 52% of theory.

EXAMPLE 26

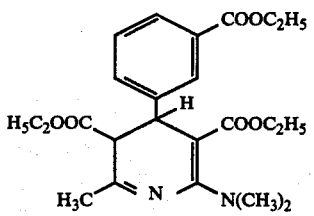

Heating a solution of 14.5 g of 3-carbethoxybenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(3-carbethoxyphenyl)-4,5-dihydropyridine-3,5-dicarboxylic acid diethyl ester as an oil.

Yield: 42% of theory.

EXAMPLE 27

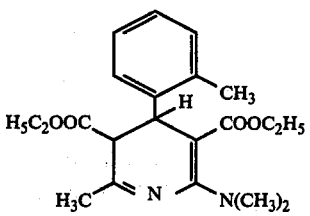

Boiling a solution of 11.6 g of 2-methylbenzylideneacetoacetic acid ethyl ester and 8.2 g of 3-amino-3-dimethylaminoacrylic acid ethyl ester in 100 ml of ethanol for 2 hours yields 2-dimethylamino-6-methyl-4-(2-methylphenyl)-4,5-dihydropyridine-3,5-dicarboxylic acid diethyl ester of melting point 88° C. (isopropanol).

Yield: 67% of theory.

EXAMPLE 28

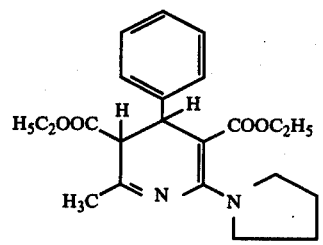

Boiling a solution of 10.9 g of benzylideneacetoacetic acid ethyl ester and 9.2 g of 3-pyrrolidino-3-aminoacrylic acid ethyl ester in 100 ml of ethanol for 2 hours and distilling the residue yields 2-pyrrolidino-6-methyl-4-phenyl-4,5-dihydropyridine-3,5-dicarboxylic acid diethyl ester of melting point 57° C. (ligroin).

Yield: 47% of theory.

What is claimed is:

1. A pharmaceutical composition useful for treating hypertension and for effecting coronary vessel dilation in animals which comprises an antihypertensive amount or a coronary-vessel-dilating amount of a compound of the formula:

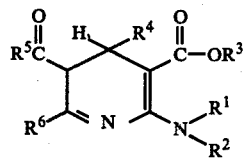

or a physiologically-acceptable acid addition salt thereof, wherein $R^1$ when taken independently is hydrogen or lower alkyl;

$R^2$ when taken independently is lower alkyl or benzyl; or $R^1$ and $R^2$ together with the nitrogen atom to which they are attached form a cyclic amine wherein $R^1$ and $R^2$ together represent alkylene of 4 to 7 carbon atoms;

$R^3$ is lower alkyl, lower alkenyl or lower alkynyl;

$R^4$ is lower alkyl; lower alkenyl; lower alkynyl; phenyl; phenyl substituted by one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio and phenyl; or naphthyl;

$R^5$ is lower alkyl, lower alkoxy, lower alkoxy(lower alkoxy), lower alkenyloxy, lower alkynyloxy, amino, lower alkylamino or di(lower alkyl)amino; and $R^6$ is hydrogen, lower alkyl or phenyl; in combination with a pharmaceutically acceptable, nontoxic diluent or carrier.

2. A composition according to claim 1 wherein $R^1$ is hydrogen, or lower alkyl;

$R^2$ is lower alkyl;

$R^3$ is lower alkyl;

$R^4$ is lower alkyl; phenyl; phenyl substituted by lower alkyl, lower alkoxy, halogeno, nitro, cyano, trifluoromethyl, carbo(lower alkoxy) or lower alkylthio; or naphthyl;

$R^5$ is lower alkyl, lower alkoxy, lower alkenyloxy or lower alkynyloxy; and $R^6$ is lower alkyl.

3. A composition according to claim 1 wherein
R¹ and R² taken together are alkylene of 4 to 6 carbon atoms;
R³ is lower alkyl;
R⁴ is lower alkyl; phenyl; phenyl substituted by lower alkyl, lower alkoxy, halogeno, nitro, cyano, trifluoromethyl, carbo(lower alkoxy) or lower alkylthio; or naphthyl;
R⁵ is lower alkyl, lower alkoxy, lower alkenyloxy or lower alkynyloxy; and
R⁶ is lower alkyl.

4. The composition according to claim 1 which is 2-piperidino-6-methyl-4-(3-nitrophenyl)-4,5-dihydropyridine-3,5-dicarboxylic acid diethyl ester.

5. The composition according to claim 1 which is 2-pyrrolidino-6-methyl-4-(3-nitrophenyl)-4,5-dihydropyridine-3,5-dicarboxylic acid 3-ethyl ester-5-methyl ester.

6. The composition according to claim 1 which is 2-pyrrolidino-6-methyl-4-(2-nitrophenyl)-4,5-dihydropyridine-3,5-dicarboxylic acid 3-ethyl ester-5-methyl ester.

7. The composition according to claim 1 which is 2-pyrrolidino-6-methyl-4-(3-nitrophenyl)-4,5-dihydropyridine-3,5-dicarboxylic acid 3-ethyl ester-5-isopropyl ester.

8. The composition according to claim 1 which is 2-piperidino-6-methyl-4-(3-nitrophenyl)-4,5-dihydropyridine-3,5-dicarboxylic acid 3-ethyl ester-5-propargyl ester.

9. The composition according to claim 1 which is 2-pyrrolidino-6-methyl-4-(3-nitrophenyl)-5-acetyl-4,5-dihydropyridine-3-carboxylic acid ethyl ester.

10. The composition according to claim 1 which is 2-perhydroazepino-6-methyl-4-(3-nitrophenyl)-4,5-dihydropyridine-3,5-dicarboxylic acid 3-ethyl ester-5-methyl ester.

11. The composition according to claim 1 which is 2-piperidino-6-methyl-4-(2-cyanophenyl)-4,5-dihydropyridine-3,5-dicarboxylic acid diethyl ester.

12. The composition according to claim 1 which is 2-pyrrolidino-6-methyl-4-(2-cyanophenyl)-4,5-dihydropyridine-3,5-dicarboxylic acid diethyl ester.

13. The composition according to claim 1 which is 2-piperidino-6-methyl-4-(2-methylphenyl)-4,5-dihydropyridine-3,5-dicarboxylic acid diethyl ester.

14. The composition according to claim 1 which is 2-pyrrolidino-6-methyl-4-(2-methoxyphenyl)-4,5-dihydropyridine-3,5-dicarboxylic acid diethyl ester.

15. The composition according to claim 1 which is 2-pyrrolidino-6-methyl-4-(2-chlorophenyl)-4,5-dihydropyridine-3,5-dicarboxylic acid diethyl ester.

16. The composition according to claim 1 which is 2-pyrrolidino-6-methyl-4-(2-trifluoromethylphenyl)-4,5-dihydropyridine-3,5-dicarboxylic acid diethyl ester.

17. The composition according to claim 1 which is 2-piperidino-6-methyl-4-(2-trifluoromethylphenyl)-4,5-dihydropyridine-3,5-dicarboxylic acid diethyl ester.

18. The composition according to claim 1 which is 2-piperidino-6-methyl-4-(4-methylmercaptophenyl)-4,5-dihydropyridine-3,5-dicarboxylic acid diethyl ester.

19. The composition according to claim 1 which is 2-dimethylamino-6-methyl-4-(3-nitrophenyl)-4,5-dihydropyridine-3,5-dicarboxylic acid diethyl ester.

20. The composition according to claim 1 which is 2-dimethylamino-6-methyl-4-(3-chlorophenyl)-4,5-dihydropyridine-3,5-dicarboxylic acid diethyl ester.

21. The composition according to claim 1 which is 2-dimethylamino-6-methyl-4-(2-trifluoromethylphenyl)-4,5-dihydropyridine-3,5-dicarboxylic acid diethyl ester.

22. The composition according to claim 1 which is 2-dimethylamino-6-methyl-4-(2-cyanophenyl)-4,5-dihydropyridine-3,5-dicarboxylic acid diethyl ester.

23. The composition according to claim 1 which is 2-dimethylamino-6-methyl-4-(3-nitrophenyl)-4,5-dihydropyridine-3,5-dicarboxylic acid 3-ethyl ester-5-methyl ester.

24. The composition according to claim 1 which is 2-pyrrolidino-4,6-dimethyl-4,5-dihydropyridine-3,5-dicarboxylic acid diethyl ester.

25. The composition according to claim 1 which is 2-pyrrolidino-6-methyl-4-(2-trifluoromethylphenyl)-4,5-dihydropyridine-3,5-dicarboxylic acid 3-isopropyl ester-5-ethyl ester.

26. The composition according to claim 1 which is 2-pyrrolidino-6-methyl-4-(3-nitrophenyl)-4,5-dihydropyridine-3,5-dicarboxylic acid 3-isopropyl ester-5-methyl ester.

27. The composition according to claim 1 which is 2-piperidino-6-methyl-4-(3-nitrophenyl)-4,5-dihydropyridine-3,5-dicarboxylic acid 3-isopropyl ester-5-methyl ester.

28. The composition according to claim 1 which is 2-pyrrolidino-6-methyl-4-naphth-1-yl-4,5-dihydropyridine-3,5-dicarboxylic acid diethyl ester.

29. The composition according to claim 1 which is 2-dimethylamino-6-methyl-4-(3-carbethoxyphenyl)-4,5-dihydropyridine-3,5-dicarboxylic acid diethyl ester.

30. The composition according to claim 1 which is 2-dimethylamino-6-methyl-4-(2-methylphenyl)-4,5-dihydropyridine-3,5-dicarboxylic acid diethyl ester.

31. The composition according to claim 1 which is 2-pyrrolidino-6-methyl-4-phenyl-4,5-dihydropyridine-3,5-dicarboxylic acid diethyl ester.

32. A method of treating hypertension in animals which comprises administering thereto an antihypertensively effective amount of a compound of the formula:

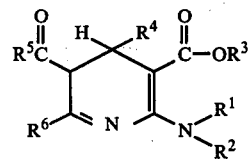

or a physiologically-acceptable acid addition salt thereof, wherein
R¹ when taken independently is hydrogen or lower alkyl;
R² when taken independently is lower alkyl or benzyl;
R¹ and R² together with the nitrogen atom to which they are attached form a cyclic amine wherein R¹ and R² together represent alkylene of 4 to 7 carbon atoms ring;
R³ is lower alkyl, lower alkenyl or lower alkynyl;
R⁴ is lower alkyl; lower alkenyl; lower alkynyl; phenyl; phenyl substituted by one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio and phenyl; or naphthyl;

$R^5$ is lower alkyl, lower alkoxy, lower alkoxy(lower alkoxy), lower alkenyloxy, lower alkynyloxy, amino, lower alkylamino or di(lower alkyl)amino; and
$R^6$ is hydrogen, lower alkyl or phenyl.

33. The method according to claim 32 wherein
$R^1$ is hydrogen, or lower alkyl;
$R^2$ is lower alkyl;
$R^3$ is lower alkyl;
$R^4$ is lower alkyl; phenyl; phenyl substituted by lower alkyl, lower alkoxy, halogeno, nitro, cyano, trifluoromethyl, carbo(lower alkoxy) or lower alkylthio; or naphthyl;
$R^5$ is lower alkyl, lower alkoxy, lower alkenyloxy or lower alkynyloxy; and
$R^6$ is lower alkyl.

34. The method according to claim 32 wherein
$R^1$ and $R^2$ taken together are alkylene of 4 to 6 carbon atoms;
$R^3$ is lower alkyl;
$R^4$ is lower alkyl; phenyl; phenyl substituted by lower alkyl, lower alkoxy, halogeno, nitro, cyano, trifluoromethyl, carbo(lower alkoxy) or lower alkylthio; or naphthyl;
$R^5$ is lower alkyl, lower alkoxy, lower alkenyloxy or lower alkynyloxy; and
$R^6$ is lower alkyl.

35. The method according to claim 32 wherein the compound is 2-piperidino-6-methyl-4-(3-nitrophenyl)-4,5-dihydropyridine-3,5-dicarboxylic acid diethyl ester.

36. The method according to claim 32 wherein the compound is 2-pyrrolidino-6-methyl-4-(3-nitrophenyl)-4,5-dihydropyridine-3,5-dicarboxylic acid 3-ethyl ester-5-methyl ester.

37. The method according to claim 32 wherein the compound is 2-pyrrolidino-6-methyl-4-(2-nitrophenyl)-4,5-dihydropyridine-3,5-dicarboxylic acid 3-ethyl ester-5-methyl ester.

38. The method according to claim 32 wherein the compound is 2-pyrrolidino-6-methyl-4-(3-nitrophenyl)-4,5-dihydropyridine-3,5-dicarboxylic acid 3-ethyl ester-5-isopropyl ester.

39. The method according to claim 32 wherein the compound is 2-piperidino-6-methyl-4-(3-nitrophenyl)-4,5-dihydropyridine-3,5-dicarboxylic acid 3-ethyl ester-5-propargyl ester.

40. The method according to claim 32 wherein the compound is 2-pyrrolidino-6-methyl-4-(3-nitrophenyl)-5-acetyl-4,5-dihydropyridine-3-carboxylic acid ethyl ester.

41. The method according to claim 32 wherein the compound is 2-perhydroazepino-6-methyl-4-(3-nitrophenyl)-4,5-dihydropyridine-3,5-dicarboxylic acid 3-ethyl ester-5-methyl ester.

42. The method according to claim 32 wherein the compound is 2-piperidino-6-methyl-4-(2-cyanophenyl)-4,5-dihydropyridine-3,5-dicarboxylic acid diethyl ester.

43. The method according to claim 32 wherein the compound is 2-pyrrolidino-6-methyl-4-(2-cyanophenyl)-4,5-dihydropyridine-3,5-dicarboxylic acid diethyl ester.

44. The method according to claim 32 wherein the compound is 2-piperidino-6-methyl-4-(2-methylphenyl)-4,5-dihydropyridine-3,5-dicarboxylic acid diethyl ester.

45. The method according to claim 32 wherein the compound is 2-pyrrolidino-6-methyl-4-(2-methoxyphenyl)-4,5-dihydropyridine-3,5-dicarboxylic acid diethyl ester.

46. The method according to claim 32 wherein the compound is 2-pyrrolidino-6-methyl-4-(2-chlorophenyl)-4,5-dihydropyridine-3,5-dicarboxylic acid diethyl ester.

47. The method according to claim 32 wherein the compound is 2-pyrrolidino-6-methyl-4-(2-trifluoromethylphenyl)-4,5-dihydropyridine-3,5-dicarboxylic acid diethyl ester.

48. The method according to claim 32 wherein the compound is 2-piperidino-6-methyl-4-(2-trifluoromethylphenyl)-4,5-dihydropyridine-3,5-dicarboxylic acid diethyl ester.

49. The method according to claim 32 wherein the compound is 2-piperidino-6-methyl-4-(4-methylmercaptophenyl)-4,5-dihydropyridine-3,5-dicarboxylic acid diethyl ester.

50. The method according to claim 32 wherein the compound is 2-dimethylamino-6-methyl-4-(3-nitrophenyl)-4,5-dihydropyridine-3,5-dicarboxylic acid diethyl ester.

51. The method according to claim 32 wherein the compound is 2-dimethylamino-6-methyl-4-(3-chlorophenyl)-4,5-dihydropyridine-3,5-dicarboxylic acid diethyl ester.

52. The method according to claim 32 wherein the compound is 2-dimethylamino-6-methyl-4-(2-trifluoromethylphenyl)-4,5-dihydropyridine-3,5-dicarboxylic acid diethyl ester.

53. The method according to claim 32 wherein the compound is 2-dimethylamino-6-methyl-4-(2-cyanophenyl)-4,5-dihydropyridine-3,5-dicarboxylic acid diethyl ester.

54. The method according to claim 32 wherein the compound is 2-dimethylamino-6-methyl-4-(3-nitrophenyl)-4,5-dihydropyridine-3,5-dicarboxylic acid 3-ethyl ester-5-methyl ester.

55. The method according to claim 32 wherein the compound is 2-pyrrolidino-4,6-dimethyl-4,5-dihydropyridine-3,5-dicarboxylic acid diethyl ester.

56. The method according to claim 32 wherein the compound is 2-pyrrolidino-6-methyl-4-(2-trifluoromethylphenyl)-4,5-dihydropyridine-3,5-dicarboxylic acid 3-isopropyl ester-5-ethyl ester.

57. The method according to claim 32 wherein the compound is 2-pyrrolidino-6-methyl-4-(3-nitrophenyl)-4,5-dihydropyridine-3,5-dicarboxylic acid 3-isopropyl ester-5-methyl ester.

58. The method according to claim 32 wherein the compound is 2-piperidino-6-methyl-4-(3-nitrophenyl)-4,5-dihydropyridine-3,5-dicarboxylic acid 3-isopropyl ester-5-methyl ester.

59. The method according to claim 32 wherein the compound is 2-pyrrolidino-6-methyl-4-naphth-1-yl-4,5-dihydropyridine-3,5-dicarboxylic acid diethyl ester.

60. The method according to claim 32 wherein the compound is 2-dimethylamino-6-methyl-4-(3-carbethoxyphenyl)-4,5-dihydropyridine-3,5-dicarboxylic acid diethyl ester.

61. The method according to claim 32 wherein the compound is 2-dimethylamino-6-methyl-4-(2-methylphenyl)-4,5-dihydropyridine-3,5-dicarboxylic acid diethyl ester.

62. The method according to claim 32 wherein the compound is 2-pyrrolidino-6-methyl-4-phenyl-4,5-dihydropyridine-3,5-dicarboxylic acid diethyl ester.

63. A method of effecting coronary vessel dilation in animals which comprises administering thereto a coronary-vessel-dilating amount of a compound of the formula

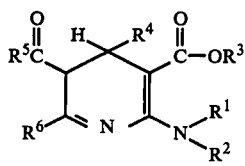

or a physiologically-acceptable acid addition salt thereof, wherein $R^1$ when taken independently is hydrogen or lower alkyl;

$R^2$ when taken independently is lower alkyl or benzyl; $R^1$ and $R^2$ together with the nitrogen atom to which they are attached form a cyclic amine wherein $R^1$ and $R^2$ together represent alkylene of 4 to 7 carbon atoms, $R^3$ is lower alkyl, lower alkenyl or lower alkynyl;

$R^4$ is lower alkyl; lower alkenyl; lower alkynyl; phenyl; phenyl substituted by one to three members selected from the group consisting of lower alkyl, lower alkoxy, halogeno, nitro, cyano, trifluoromethyl, azido, carbo(lower alkoxy), lower alkylsulfonyl, lower alkylsulfinyl, lower alkylthio or phenyl; or naphthyl;

$R^5$ is lower alkyl, lower alkoxy, lower alkoxy(lower alkoxy), lower alkenyloxy, lower alkynyloxy, amino, lower alkylamino or di(lower alkyl)amino; and $R^6$ is hydrogen, lower alkyl or phenyl.

64. The method according to claim 63 wherein $R^1$ is hydrogen, or lower alkyl;

$R^2$ is lower alkyl;

$R^3$ is lower alkyl;

$R^4$ is lower alkyl; phenyl; phenyl substituted by lower alkyl, lower alkoxy, halogeno, nitro, cyano, trifluoromethyl, carbo(lower alkoxy) or lower alkylthio; or naphthyl;

$R^5$ is lower alkyl, lower alkoxy, lower alkenyloxy or lower alkynyloxy; and $R^6$ is lower alkyl.

65. The method according to claim 63 wherein $R^1$ and $R^2$ taken together are alkylene of 4 to 6 carbon atoms;

$R^3$ is lower alkyl;

$R^4$ is lower alkyl; phenyl; phenyl substituted by lower alkyl, lower alkoxy, halogeno, nitro, cyano, trifluoromethyl, carbo(lower alkoxy) or lower alkylthio; or naphthyl;

$R^5$ is lower alkyl, lower alkoxy, lower alkenyloxy or lower alkynyloxy; and $R^6$ is lower alkyl.

66. The method according to claim 63 wherein the compound is 2-piperidino-6-methyl-4-(3-nitrophenyl)-4,5-dihydropyridine-3,5-dicarboxylic acid diethyl ester.

67. The method according to claim 63 wherein the compound is 2-pyrrolidino-6-methyl-4-(3-nitrophenyl)-4,5-dihydropyridine-3,5-dicarboxylic acid 3-ethyl ester-5-methyl ester.

68. The method according to claim 63 wherein the compound is 2-pyrrolidino-6-methyl-4-(2-nitrophenyl)-4,5-dihydropyridine-3,5-dicarboxylic acid 3-ethyl ester-5-methyl ester.

69. The method according to claim 63 wherein the compound is 2-pyrrolidino-6-methyl-4-(3-nitrophenyl)-4,5-dihydropyridine-3,5-dicarboxylic acid 3-ethyl ester-5-isopropyl ester.

70. The method according to claim 63 wherein the compound is 2-piperidino-6-methyl-4-(3-nitrophenyl)-4,5-dihydropyridine-3,5-dicarboxylic acid 3-ethyl ester-5-propargyl ester.

71. The method according to claim 63 wherein the compound is 2-pyrrolidino-6-methyl-4-(3-nitrophenyl)-5-acetyl-4,5-dihydropyridine-3-carboxylic acid ethyl ester.

72. The method according to claim 63 wherein the compound is 2-perhydroazepino-6-methyl-4-(3-nitrophenyl)-4,5-dihydropyridine-3,5-dicarboxylic acid 3-ethyl ester-5-methyl ester.

73. The method according to claim 63 wherein the compound is 2-piperidino-6-methyl-4-(2-cyanophenyl)-4,5-dihydropyridine-3,5-dicarboxylic acid diethyl ester.

74. The method according to claim 63 wherein the compound is 2-pyrrolidino-6-methyl-4-(2-cyanophenyl)-4,5-dihydropyridine-3,5-dicarboxylic acid diethyl ester.

75. The method according to claim 63 wherein the compound is 2-piperidino-6-methyl-4-(2-methylphenyl)-4,5-dihydropyridine-3,5-dicarboxylic acid diethyl ester.

76. The method according to claim 63 wherein the compound is 2-pyrrolidino-6-methyl-4-(2-methoxyphenyl)-4,5-dihydropyridine-3,5-dicarboxylic acid diethyl ester.

77. The method according to claim 63 wherein the compound is 2-pyrrolidino-6-methyl-4-(2-chlorophenyl)-4,5-dihydropyridine-3,5-dicarboxylic acid diethyl ester.

78. The method according to claim 63 wherein the compound is 2-pyrrolidino-6-methyl-4-(2-trifluoromethylphenyl)-4,5-dihydropyridine-3,5-dicarboxylic acid diethyl ester.

79. The method according to claim 63 wherein the compound is 2-piperidino-6-methyl-4-(2-trifluoromethylphenyl)-4,5-dihydropyridine-3,5-dicarboxylic acid diethyl ester.

80. The method according to claim 63 wherein the compound is 2-piperidino-6-methyl-4-(4-methylmercaptophenyl)-4,5-dihydropyridine-3,5-dicarboxylic acid diethyl ester.

81. The method according to claim 63 wherein the compound is 2-dimethylamino-6-methyl-4-(3-nitrophenyl)-4,5-dihydropyridine-3,5-dicarboxylic acid diethyl ester.

82. The method according to claim 63 wherein the compound is 2-dimethylamino-6-methyl-4-(3-chlorophenyl)-4,5-dihydropyridine-3,5-dicarboxylic acid diethyl ester.

83. The method according to claim 63 wherein the compound is 2-dimethylamino-6-methyl-4-(2-trifluoromethylphenyl)-4,5-dihydropyridine-3,5-dicarboxylic acid diethyl ester.

84. The method according to claim 63 wherein the compound is 2-dimethylamino-6-methyl-4-(2-cyanophenyl)-4,5-dihydropyridine-3,5-dicarboxylic acid diethyl ester.

85. The method according to claim 63 wherein the compound is 2-dimethylamino-6-methyl-4-(3-nitrophenyl)-4,5-dihydropyridine-3,5-dicarboxylic acid 3-ethyl ester-5-methyl ester.

86. The method according to claim 63 wherein the compound is 2-pyrrolidino-4,6-dimethyl-4,5-dihydropyridine-3,5-dicarboxylic acid diethyl ester.

87. The method according to claim 63 wherein the compound is 2-pyrrolidino-6-methyl-4-(2-trifluoromethylphenyl)-4,5-dihydropyridine-3,5-dicarboxylic acid 3-isopropyl ester-5-ethyl ester.

88. The method according to claim 63 wherein the compound is 2-pyrrolidino-6-methyl-4-(3-nitrophenyl)-4,5-dihydropyridine-3,5-dicarboxylic acid 3-isopropyl ester-5-methyl ester.

89. The method according to claim 63 wherein the compound is 2-piperidino-6-methyl-4-(3-nitrophenyl)-4,5-dihydropyridine-3,5-dicarboxylic acid 3-isopropyl ester-5-methyl ester.

90. The method according to claim 63 wherein the compound is 2-pyrrolidino-6-methyl-4-naphth-1-yl-4,5-dihydropyridine-3,5-dicarboxylic acid diethyl ester.

91. The method according to claim 63 wherein the compound is 2-dimethylamino-6-methyl-4-(3-carbethoxyphenyl)-4,5-dihydropyridine-3,5-dicarboxylic acid diethyl ester.

92. The method according to claim 63 wherein the compound is 2-dimethylamino-6-methyl-4-(2-methylphenyl)-4,5-dihydropyridine-3,5-dicarboxylic acid diethyl ester.

93. The method according to claim 63 wherein the compound is 2-pyrrolidino-6-methyl-4-phenyl-4,5-dihydropyridine-3,5-dicarboxylic acid diethyl ester.

* * * * *